United States Patent
Xie (10) Patent No.: US 9,234,420 B2
(45) Date of Patent: Jan. 12, 2016

(54) IMMERSION PROBE USING ULTRAVIOLET AND INFRARED RADIATION FOR MULTI-PHASE FLOW ANALYSIS

(75) Inventor: Cheng-Gang Xie, Sawston (GB)

(73) Assignee: Schlumberger Technology Corporation, Houston, TX (US)

( * ) Notice: Subject to any disclaimer, the term of this patent is extended or adjusted under 35 U.S.C. 154(b) by 331 days.

(21) Appl. No.: 13/516,688

(22) PCT Filed: Dec. 17, 2010

(86) PCT No.: PCT/IB2010/003293
§ 371 (c)(1),
(2), (4) Date: Oct. 1, 2012

(87) PCT Pub. No.: WO2011/073789
PCT Pub. Date: Jun. 23, 2011

(65) Prior Publication Data
US 2013/0016336 A1   Jan. 17, 2013

Related U.S. Application Data

(60) Provisional application No. 61/288,048, filed on Dec. 18, 2009, provisional application No. 61/288,371, filed on Dec. 21, 2009.

(51) Int. Cl.
*G01J 5/00* (2006.01)
*E21B 49/08* (2006.01)
(Continued)

(52) U.S. Cl.
CPC ............. *E21B 49/087* (2013.01); *G01N 21/33* (2013.01); *G01N 21/3504* (2013.01);
(Continued)

(58) Field of Classification Search
CPC .... G01N 21/3504; G01N 21/05; G01N 30/74
USPC ............................................ 250/338.1–338.5
See application file for complete search history.

(56) References Cited

U.S. PATENT DOCUMENTS 5,528,039 A * 6/1996 Bernard ........................ 250/343
5,663,559 A 9/1997 Auzerais et al.
(Continued)

FOREIGN PATENT DOCUMENTS

| GB | 2406386 B | 3/2007 |
|----|-----------|--------|
| GB | 2426579 B | 1/2008 |

(Continued)

OTHER PUBLICATIONS

Nagali et al., "Design of a diode-laser sensor to monitor water vapor in high pressure combustion gases," 1997, Applied Physics, vol. 36, No. 36, pp. 9518-9527.*

(Continued)

*Primary Examiner* — Kiho Kim (57) ABSTRACT

A system and method for determining characteristics of a multiphase flow in a well/pipe are disclosed. The disclosed system and method use an optical immersion probe including a flow gap across which two or more types of radiation are transmitted in order to measure absorptions of two or more substances within the multiphase flow. Primarily, broadband ultraviolet (UV) and/or near infrared radiations (NIR) are utilized with the probe to gather absorption data at and/or around at least one of the water peaks and at and/or around one or more oil or oil-condensate peaks. This data may be utilized to calculate the water-cut of the multiphase flow over a wider range of gas volume fractions. Additionally, pressure ports having pressure sensors being located on the optical immersion probe for determining the impact pressures and flow rates of different phases of the multiphase flow may also be used.

20 Claims, 5 Drawing Sheets

(51) Int. Cl.

| | | |
|---|---|---|
| *G01N 21/33* | (2006.01) | |
| *G01N 21/85* | (2006.01) | |
| *G01N 21/3504* | (2014.01) | |
| *G01V 3/30* | (2006.01) | |
| *G01V 8/22* | (2006.01) | |
| G01N 21/359 | (2014.01) | |
| G01N 21/05 | (2006.01) | |
| G01N 21/3577 | (2014.01) | |
| G01J 3/28 | (2006.01) | |

(52) U.S. Cl.
CPC ............ *G01N 21/8507* (2013.01); *G01V 3/30* (2013.01); *G01V 8/22* (2013.01); *G01J 3/28* (2013.01); *G01N 21/05* (2013.01); *G01N 21/359* (2013.01); *G01N 21/3577* (2013.01)

(56) References Cited

U.S. PATENT DOCUMENTS

| | | | |
|---|---|---|---|
| 6,292,756 | B1 | 9/2001 | Lievois et al. |
| 6,564,865 | B1* | 5/2003 | Brady et al. ............... 166/105.3 |
| 6,588,266 | B2 | 7/2003 | Tubel et al. |
| 6,831,470 | B2 | 12/2004 | Xie et al. |
| 6,954,560 | B2* | 10/2005 | Tolmachev et al. ............. 385/12 |
| 7,650,799 | B2 | 1/2010 | Atkinson et al. |
| 7,717,000 | B2 | 5/2010 | Xie et al. |
| 7,804,598 | B2 | 9/2010 | Hall et al. |
| 7,942,065 | B2 | 5/2011 | Xie |
| 8,027,794 | B2 | 9/2011 | Xie |
| 2002/0066309 | A1 | 6/2002 | Tubel et al. |
| 2003/0030799 | A1* | 2/2003 | Chen et al. .................... 356/300 |
| 2004/0043501 | A1 | 3/2004 | Means et al. |
| 2005/0039544 | A1* | 2/2005 | Jones ............................. 73/861 |
| 2007/0114372 | A1 | 5/2007 | Lievois et al. |
| 2008/0043240 | A1 | 2/2008 | Reminiac et al. |
| 2009/0204346 | A1 | 8/2009 | Xie |
| 2009/0216463 | A1 | 8/2009 | Xie et al. |
| 2009/0229375 | A1 | 9/2009 | Atkinson et al. |
| 2010/0299088 | A1 | 11/2010 | Huang et al. |
| 2010/0315645 | A1 | 12/2010 | Hall et al. |

FOREIGN PATENT DOCUMENTS

| | | |
|---|---|---|
| GB | 2432425 B | 1/2008 |
| GB | 2431010 C | 5/2008 |
| GB | 2447490 B | 5/2009 |
| KR | 2009090616 A | 8/2009 |

OTHER PUBLICATIONS

International Search Report of PCT Application No. PCT/IB2010/003294 dated Jun. 27, 2011.

Sato et al., "Hydrophobic hydration and molecular association in methanol-water mixtures studied by microwave dielectric analysis," J. Chem. Phys., 2000, vol. 112(6): pp. 2924-2932.

Cho et al., "Determination of Water Content in Ethanol by Miniaturized Near-Infrared (NIR) System," Bull. Korean Chem. Soc., 2005, vol. 26(1): pp. 115-118.

Hall et al., "Paper 5.2: Testing of the Red Eye Near-Infrared Water Cut Monitor in High GVF Multiphase Flow Conditions," 6th International South East Asia Hydrocarbon Flow Measurement Workshop, Mar. 2007: pp. 1-25.

Katsumoto et al., "Usefulness of a curve fitting method in teh analysis of overlapping overtones and combinations of CH stretching modes," J. Near Infrared Spectrosc., 2002, vol. 10: pp. 85-91.

Lin et al., "Simultaneous determination of physical and chemical properties of sodium chloride solutions by near infrared spectroscopy," J. Near Infrared Spectrosc., 1993, vol. 1: pp. 109-120.

Sato et al., "Dynamical aspects of mixing schemes in ethanol-water mixtures in terms of the excess partial molar activation free energy, enthalpy, and entropy of the dielectric relaxation process," J. Chem. Phys., 1999, vol. 110(5): pp. 2508-2521.

* cited by examiner

IMMERSION PROBE USING ULTRAVIOLET AND INFRARED RADIATION FOR MULTI-PHASE FLOW ANALYSIS

CROSS-REFERENCE TO RELATED APPLICATIONS

This application is a U.S. National Stage Application under 35 U.S.C. 371 which claims priority to PCT Application No. PCT/IB2010/003293 filed Dec. 17, 2010 which claims benefit of U.S. Provisional Patent Application Ser. No. 61/288,371 filed Dec. 21, 2009 and U.S. Provisional Patent Application Ser. No. 61/288,048 filed Dec. 18, 2009, all of which are incorporated herein by reference in their entireties.

BACKGROUND

This disclosure relates in general to immersion probes and, but not by way of limitation, to using immersion probes for measuring the water-cut in gas-condensate (wet-gas) wells, amongst other things.

Probes, such as immersion probes, can offer a range of data which aids in both determining and helping to regulate the content and/or flow rate of gas and oil flows in wells. Use of these probes varies dependent on the type of well in which it is utilized. For instance, natural gas and crude oil wells vary in the amount of gas-condensate, oil, natural gas, water and gas volume fractions (GVF) that are present. Accordingly, the probes are designed to accommodate such differences in order to provide the most accurate readings of the constituents within each well type.

Currently, the primary optical technique for determining the water-cut is utilizing a near infrared (NIR) beam to measure absorption levels in the multi-phase mixtures for oil/gas-condensate wells having low to high gas volume fractions. Water-cut may also be referred to as water-in-liquid ratio (WLR) for a well-mixed liquid and is the amount of water content in the liquid phase of a multiphase flow. The NIR beam is utilized because water is highly absorbed in the NW range, with one of the peak absorptions at around 1450 nanometers (nm). The absorption of oils, condensate and water mixtures varies, each can have relatively different absorptions at different wavelengths. For instance, oil-condensate or light oils show higher absorptions at lower wavelengths and water shows absorption peaks at higher wavelengths.

Prior art configurations for determining the water cut of a flow, use a probe disposed along the two opposing sides of a well pipe and having a beam sent across the pipe from an NIR and/or ultraviolet (UV) light source to a receiving element separated by the diameter of the pipe. The received light is then sent to an NIR and/or UV spectrometer and the results are processed by a computer or other device having a capability to perform spectral analysis. The spectrally analyzed results from the aforementioned configuration, which configuration is disclosed in the commonly owned GB Patent Number GB2426579B, provide for analyzing the presence of water and/or oil condensate in the liquid phase of gas-condensate multi-phase wells. As previously mentioned, the near infrared light at a selected wavelength band is highly absorbed by water, and has close to zero absorption by the gas and gas condensate. The UV light at a selected wavelength band, on the other hand, is highly absorbed by condensate oil and is substantially transparent to the gas and water.

The aforementioned technique is limited to sensing the liquid fractions across the diameter of a pipe for flows of very high GVF or very low liquid fractions, as well as provides presence of water and/or oil condensate in a multiphase flow. However, the actual quantitative water-cut measurements can be problematic in these systems as GVF decreases or as the liquid fraction increases. This is primarily due to the increased scattering attenuation effect cross pipe which may overwhelm the underlying small absorption measurements used to extract liquid fractions. The scattering effect occurs from entrained liquid droplets and bubbles within the gas phase flow and liquid phase flow, respectively. Further, additional problems occur when the light source is inconsistent. In some systems, the light sources are integrated into the insertion sensing probe itself and exposed directly to the high temperature and pressure conditions of the flows in a well pipe. These light sources, such as light emitting diodes (LED), become degraded and produce shifted wavelength bands at different temperatures and over the lifetime of the device. Accordingly, such faulty light sources require removal and replacement of the entire sensing probe system.

BRIEF SUMMARY

The present embodiments provide a system and method for determining characteristics of a multiphase flow in a well pipe. The embodiments further provide an optical immersion probe including a flow gap across which two or more types of radiation are transmitted to determine absorptions of two or more substances within a multiphase flow. In certain aspects, broadband ultraviolet (UV) and/or near infrared radiation (NIR) may be utilized to gather absorption data at and/or around at least one of the water peaks and at and/or around one or more oil or oil-condensate peaks. This data may be utilized to calculate the water-cut of the multiphase flow over a wide range of gas volume fractions. Additional embodiments may include pressure ports having pressure sensors being located on the optical immersion probe, for determining the impact pressures and flow rates of different phases of the multiphase flow. In some embodiments, to improve flow rate measurements, the flow may be separated into phases by swirling the flow to form a liquid annulus at the inner wall of a pipe and a gas core at the pipe centre.

In one embodiment, the present disclosure provides an optical immersion probe for analyzing a multiphase flow in a pipe. The optical immersion probe includes a housing and, one or more first optical conduits which carry ultraviolet radiation and/or infrared radiation from one or more radiation sources at a first end to a second end. The optical immersion probe also includes a flow gap across which the ultraviolet radiation and/or the infrared radiation is transmitted. The flow gap may be adjustable, and begins at the second end of the one or more first optical conduits and is configured to operatively engage the multiphase flow within the pipe. The optical immersion probe also includes one or more second optical conduits, which is adapted to receive at least a portion of the ultraviolet radiation and/or infrared radiation and transmit at least a portion of the ultraviolet radiation and/or infrared radiation to one or more spectrometers for spectral analysis. The ultraviolet radiation and/or infrared radiation is attenuated through absorption and/or scattering by the multiphase flow in the flow gap. The multiphase flow is then analyzed through the ultraviolet radiation and/or infrared radiation attenuation determined by the spectrometers.

In some embodiments, the optical immersion probe includes a reflective element for reflecting the ultraviolet radiation and/or the infrared radiation across the multiphase flow from the one or more first optical conduits to the one or more second optical conduits. In other embodiments, the optical immersion probe includes an optical window through which to send and receive the ultraviolet radiation and/or infrared radiation. In certain aspects, the optical window may be collimated. The optical immersion probe may also include one or more pressure sensors for measuring impact pressure of at least one of the phases in the multiphase flow in some embodiments. The optical immersion probe may also include one or more ports for exposing the one or more pressure sensors through one or more pressure lines to the multiphase flow. The one or more pressure lines may be used to measure a density of one or more phases of the multiphase flow. In some aspects, the ports of the pressure sensors may be separated by a distance substantially equal to the pipe radius.

In another embodiment, a method is provided for analyzing the multiphase flow in the pipe. The method includes carrying ultraviolet and/or infrared radiation from one or more light sources in one or more first optical conduits, transmitting the ultraviolet and/or infrared radiation from the one or more first optical conduits across a flow gap. In one embodiment, the flow gap begins at the second end of the one or more first optical conduits and is configured to operatively engage the multiphase flow. The method may further include reflecting the ultraviolet and/or infrared radiation on a reflective element, where the reflective element may be located a distance across the flow gap from the one or more first optical conduits. In certain embodiments, the method may include receiving at least a portion of the reflected ultraviolet and/or infrared radiation in a second optical conduit, transmitting at least a portion of the received ultraviolet and/or infrared radiation to one or more optical spectrometers for spectral analysis, and analyzing the multiphase flow in a computing/processing device to determine characteristics of the multiphase flow. The ultraviolet radiation and/or infrared radiation is attenuated through absorption and/or scattering when in contact with the multiphase flow. In aspects of the present invention, the multiphase flow is analyzed through the ultraviolet and/or infrared attenuations determined by the spectrometers.

In some embodiments, the multiphase flow includes at least a gas phase and a liquid phase, the liquid phase comprising one or more of water and oil condensate. The method can further include swirling the multiphase flow to separate the gas and liquid phases of the flow, wherein the swirling comprises applying a centrifugal force. Merely by way of example, the one or more spectrometers may include an infrared spectrometer operating at the 900-2550 nanometer range. Merely by way of example, the one or more spectrometers may include an ultraviolet spectrometer operating at the 200-800 nanometer range. In some embodiments, the one or more radiation sources may be located external to and separate from the optical insertion probe. In certain aspects, the one or more radiation sources may include a first radiation source capable of emitting a continuous light spectrum across/within the ultraviolet to visible range. In some embodiments, the one or more radiation sources may include a second radiation source capable of emitting a continuous light spectrum within/in the visible to near infrared range.

In another embodiment, a method for analyzing a multiphase flow in a pipe with an optical immersion probe is provided. The method includes carrying ultraviolet and/or infrared radiation from one or more light sources in one or more first optical conduits, transmitting the ultraviolet and/or infrared radiation from the one or more first optical conduits across a flow gap, which is configured to operatively engage at least one phase of the multiphase flow, and reflecting the ultraviolet and/or infrared radiation on a reflective element. The reflective element being located a distance across the flow gap from the one or more first optical conduits. The method may further include receiving at least a portion of the reflected ultraviolet and/or infrared radiation in a second optical conduit and transmitting at least a portion of the received ultraviolet and/or infrared radiation to one or more optical spectrometers for spectral analysis.

In some embodiments, the method includes applying centrifugal force to the multiphase flow. The centrifugal force effectively separates one or more phases of the flow. In other embodiments, the method further includes exposing one or more pressure sensors to the multiphase flow and measuring the impact pressure of the one or more phases in the multiphase flow with the one or more pressure sensors. Merely by way of example, the one or more first optical conduits can be an optical fiber bundle for transmitting radiation. The one or more second optical conduits can be an optical fiber bundle for receiving radiation. The ultraviolet radiation may comprise broadband ultraviolet to visible radiation in one embodiment. The infrared radiation may comprise broadband visible to infrared radiation in a further embodiment.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures.

In the appended figures, similar components and/or features may have the same reference label. Where the reference label is used in the specification, the description is applicable to any one of the similar components having the same reference label.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes can be made in the function, and arrangement of elements without departing from the scope as set forth in the appended claims.

In one embodiment of the present invention, an apparatus and method for measuring liquid hold-up across a flow path primarily for use in gas-condensate wells is disclosed. In aspects of the present invention, an optical immersion probe that utilizes two radiation beams to measure water in liquid ratio (WLR), or water-cut, of a multiphase flow over a wide range of GVFs in the gas-condensate wells across a flow gap within the optical immersion probe is provided. By way of example, in the embodiment, both beams may be transmitted across substantially the same portion of the multiphase flow.

In certain aspects, the optical immersion probe may utilize a first ultraviolet (UV) light source as an interrogation beam to measure gas condensate content. Gas condensate, which can be interchangeably referred to as light oil or oil condensate, is a low density hydrocarbon liquid product of raw natural gas wells, or wet-gas, wells. In the UV spectrum range, gas condensate is highly absorbing, having an absorption peak, for instance, at around 280 nanometers (nm). The gaseous and the water phases are substantially transparent, in terms of optical absorption, in the UV spectrum range.

The optical immersion probe may in some embodiments also utilize a second near infrared (NIR) light source as a second interrogation beam to measure water content in the liquid phase of the multiphase flow. Water may be a by-product present in the multiphase flow that usually increases in content over time within the well due to, for example, formation water breakthrough. The water can mix with the light oil to form a liquid phase mixture in multi-phase flows produced from a well. The higher the flow rate in the well, the more well mixed two liquids may become in the multiphase flow. In the NIR spectrum range, water is highly absorbing, having one of the absorption peaks, for instance, at around 1450 nm. At and/or around this absorption peak, the gaseous and the gas-condensate phases are substantially transparent.

The addition of the UV light source to the optical immersion probe, in accordance with an embodiment of the present invention, allows for the amount and presence of the gas condensate to be measured in addition to the water in the gas condensate within the well pipe. This measurement is possible because gas condensate, or light oil, is highly absorbed/absorbing in the UV light spectrum range, whereas gaseous and the water phases are substantially transparent. In one embodiment, when both the UV and IR absorptions along substantially the same optical path are calculated, a ratio of the volume fractions of the two liquids may be derived in order to provide an improved measurement of the water-cut and/or WLR. Utilizing both UV and IR light may allow for determining an optical density (absorption) contrast between the water and the gas-condensate in the multiphase flow, resulting in a WLR measurement with a higher tolerance to scattering attenuation effects caused by liquid droplets and/or gas bubbles, especially at high GVFs The use of such UV light is further discussed in commonly owned GB patent number GB2426579B, which is hereby incorporated by reference in its entirety. UV fluorescence spectroscopy measurement may also be used for improved identification and measurement of oil properties.

In certain embodiments, light sources providing continuous light emission over a broadband spectrum of both UV and NIR light and/or the visible spectrum range may also be included. A broadband spectrum may be utilized in order to take into account the scattering attenuation effect at multiple absorption wavelengths in addition to the changes in the absorption properties of the oil and/or water at different temperatures and pressures. In an embodiment of the present invention, the light sources and the spectrometers may be located external to the optical immersion probe itself and the composite UV/NIR/Vis light may be guided from the sources through optical fiber bundles which are coupled to an optical window within the optical immersion probe. The optical immersion probe may include a flow gap across which the light is transmitted. In certain aspects, the light is reflected back through the optical immersion probe and guided by the receiving optics and optical fiber bundles into spectrometers where spectral analyses may be performed.

In further embodiments, the optical immersion probe may additionally contain temperature and/or pressure sensors, which may aid in determining the flow thermodynamic conditions, measuring static and/or dynamic pressures, velocity, flow rates and content of the multiphase flow within the well. In some aspects, the multiphase flow may be separated through swirling the flow and using centrifugal force to cause the flow to form a liquid annulus on the inner wall of the pipe and a gas core in the center of the pipe. The swirling technique is further discussed in the commonly owned U.S. Pat. No. 7,650,799, which is hereby incorporated by reference in its entirety. The multiphase flow separation may be useful for the measurement of flow velocities and flow rates of each of the respective phases of the multiphase flow. Accordingly, in certain aspects, additional elements, such as pressure ports, may be added along the body of the optical immersion probe in order to collect impact pressure readings for the calculation of flow rates and velocities in specified areas in the pipe. The aforementioned embodiments are further described with reference to the figures in the paragraphs that follow.

Figure 1:
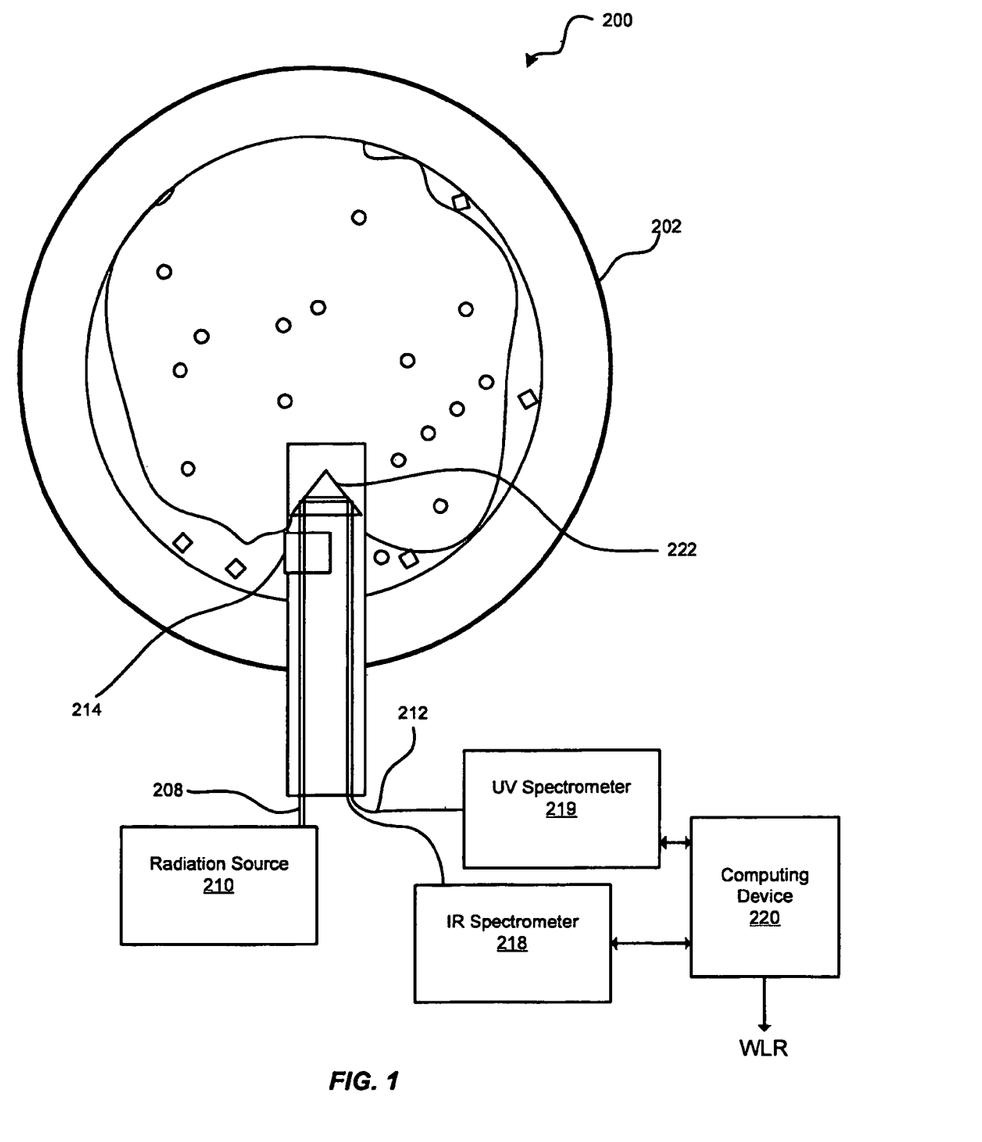
FIG. 1 provides an illustration of a system including an optical immersion probe for use in a multiphase flow, in accordance with an embodiment of the present invention.
Figure 2A:
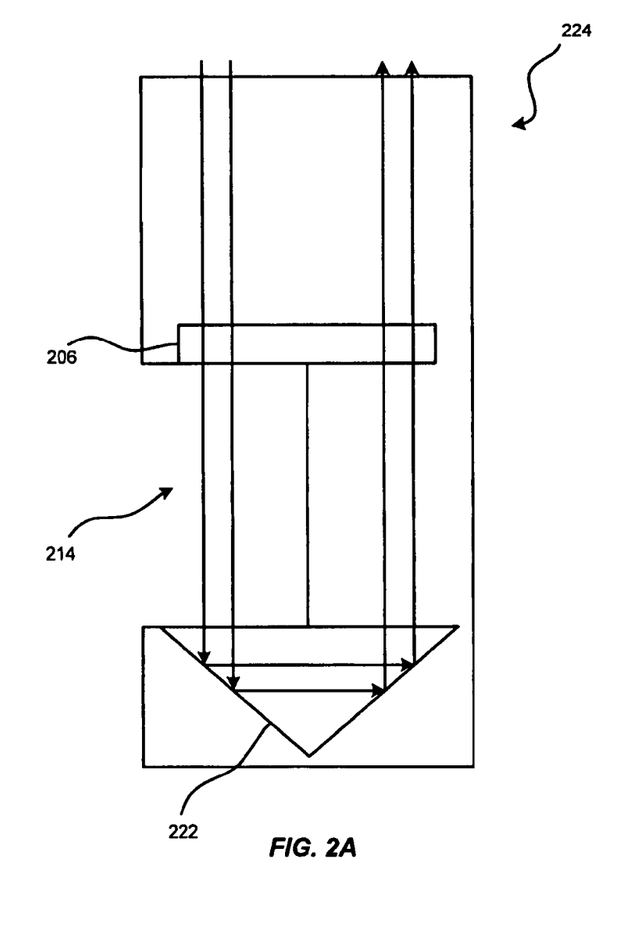
FIG. 2A provides a configuration for an optical immersion probe having a single optical radiation path, in accordance with an embodiment of the present invention.

Referring now to FIG. 1, an embodiment of the present invention provides an optical immersion probe 200 for insertion into a pipe 202 of a gas-condensate well. The optical immersion probe 200 may include an optical window 206 (shown in FIG. 2) through which fiber optic bundles 208 transfer both near infrared light (NIR) and ultraviolet light (UV) from external light source(s) 210. The NIR and UV light can also be referred to as NIR and UV radiation, and are in and of the same element within this disclosure.

The transmitting optical fiber bundle(s) 208 contains fibers optimized for efficient transmission of both UV and NIR radiation. The optical fiber bundle(s) can be treated to reduce the darkening and/or solarization effect, which effect hinders light transmission. In addition, the fiber bundles can be designed to aid in the particular, UV/vis or vis/IR, radiation transmittance. Such radiation transmittance can be referred to as radiation, light, light beams, or any combination thereof.

The light beams travel through a flow gap 214 across the multiphase mixture, which can include multiphase flows, such as three (3) phase wet-gas flows containing light oil or oil condensate, water, gas and other substances. The separation of the flow gap 214 can be adjustable in certain aspects. In some embodiments, the light beams may be produced by separate light sources and/or a composite light source that are able to radiate light at various wavelengths in a single spectrum or across a broad spectrum. Merely by way of example, the light source may comprise a deuterium lamp (200-400 nm) capable of producing vis/UV light, and/or a halogen lamp (360-2000 nm) capable of producing vis/NIR light. Any other source of radiation known within the art may also be utilized.

The optical immersion probe 200 may contain an optical window 206 (shown in FIG. 2) across the flow gap through which the light may travel. In certain aspects, the fiber bundles do not come in contact with the multiphase flow and transmit light through the optical windows 206, which are high pressure sealed for protection against the possible high pressures and temperatures of the flow. The optical window may comprise a suitable type of material, such as natural or synthetic sapphire, to allow for transmission of UV/Vis/NIR light, hence allowing the reflected light to travel from the gap to the receiving optical fibers 212.

In an embodiment of the present invention, the light is reflected by a reflective element 222, such as a prism, mirror, white tile or similar reflecting means, capable of reflecting at least a portion of the transmitted light into either a single path or double path arrangement. As shown in FIG. 2 A (and in FIG. 1), a single path optical immersion probe is illustrated, having a prism 222 as a reflective element. The reflected light may be gathered into secondary optical fiber bundle 212 adapted to receive the reflected light. As with the first optical fiber bundle, the second bundle may also be treated to reduce the darkening and/or solarization effect and may also be designed for functioning with the wavelength of radiation to be transmitted. The secondary optical fiber bundle 212 guides the reflected light to both of a UV spectrometer 218 and an NIR spectrometer 219, which in aspects of the present invention may be in connection with a computing device 220 for performing spectral analysis.

Figure 2B:
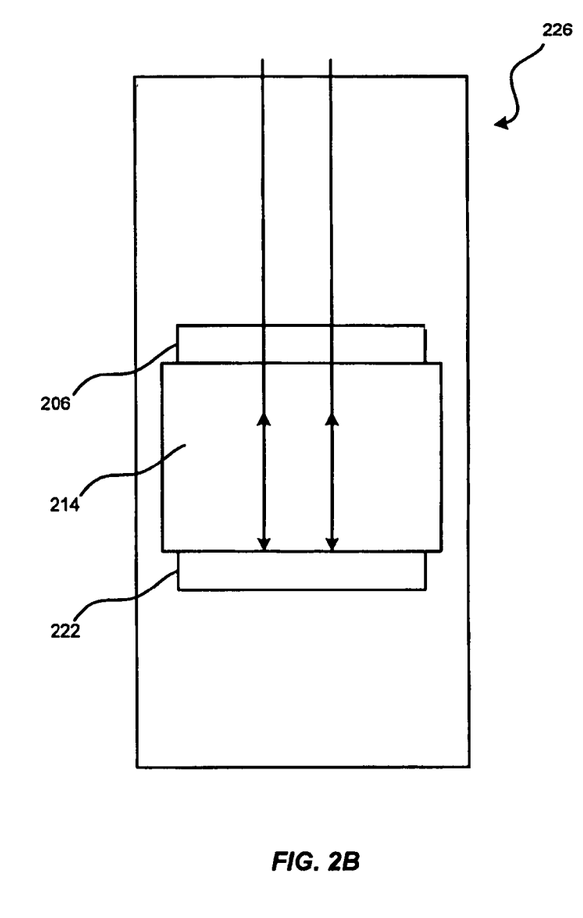
FIG. 2B provides a configuration for an optical immersion probe having a double optical radiation path, in accordance with an embodiment of the present invention.

Referring now to FIGS. 2A and 2B, arrangements for a single path 224 and double path 226 optical immersion probe are illustrated, respectively. The single path 224 optical immersion probe provides a single transmitted light path across the flow gap 214, which is reflected by a prism 222. The light is transmitted through optical window 206 and reflected back through the optical immersion probe body for collection by the second optical fiber bundle. Accordingly, the single path optical immersion probe has an optical path length substantially equal to the length of the flow gap, as the light only travels through the flow across the length of the flow gap 214 once. Conversely, the double path optical immersion probe 226 has an optical path length substantially equal to twice the length of the flow gap. This is because the light is transmitted through the flow in the flow gap 214 a first time, reflected by a reflective element 222 and sent through the flow in the flow gap 214 a second time. The flow gap 214 can be adjusted to a desired separation.

As previously mentioned, in accordance with embodiments of the present invention, the optical immersion probe utilizes single path 224 or double path 226 techniques as shown in FIGS. 2A and 2B, respectively, in order to collect optical attenuation data. However, a single path 224 optical immersion probe, where the flow path is equal to the light path (i.e., optical path is equal to the physical path length), will minimize optical attenuation from the scattering effect across the same flow path-length, or gap size in the optical immersion probe. In addition, the single path 224 optical immersion probe provides better linearity in terms of minimizing spectral stray light. This is because an available spectrometer operating range is more linear at or below an optical density (OD) equal to three. For example, if the optical immersion probe is a double path 226 probe of a 1-mm flow gap (2-mm optical path length) filled with pure water, the measured OD=~3.2 at 1450 nm NIR water-peak wavelength, whereas the single path 224 probe of the same 1-mm flow gap will measure OD=~1.6. Accordingly, the single path optical immersion probe better utilizes the full optical-density measurement range of the optical spectrometers to deal with both the absorption and scattering effects of a multiphase flow.

In addition, the oil/water liquid fraction data is more linear when the raw optical-absorption spectroscopic measurements with sufficient signal-to-noise ratio are taken over short time intervals (e.g., 1 ms), due to the dynamic flow effects when a multiphase flow passes through the flow gap. This is because the liquid fraction is a logarithmic, hence a nonlinear function, of the optical absorption. The logarithm of the time-average of optical absorptions will be an underestimate of the desired time-average of the logarithm of optical absorptions, if the underlying optical-absorption process changes much faster in time than the data collection sampling rate, due to for example, scattering effects of bubbles and droplets passing through the flow gap. Accordingly, the continuous and rapid data collection over a broadband wavelength range, which covers the entire water absorption peak at 1450 nm within 900-1750 nm (NIR) and the entire oil absorption peak (or high values near the oil peak) typically within 200-400 nm (UV), allows for a more accurate characterization of the absorption peaks of water and oil. When such measurements are taken, changes in wavelength and/or in magnitude in the absorption peaks due to changes in pressure and temperature of the flow can be fully captured by broadband spectroscopy; changes in the optical-density baseline due to scattering variations can also be better captured and removed.

The two readings (i.e., UV, IR) at different broadband wavelengths allow for a baseline, and/or reference measurement, to be taken for each type of liquid substance (i.e., water, light oil) thereby allowing baseline-shifted absorption peaks to be seen. Thus, the water and gas condensate, or light oil compositions may be better characterized if both demonstrate similar baseline shift due to scattering attenuation, or variations in pressure, temperature or substance composition (e.g., hydrate-inhibitor methanol additive).

Accordingly, in some aspects of the present invention, the rapid and continuous measurements of the oil and water absorption peaks and their baselines over a broadband of wavelengths may be utilized to correct for the effects caused by water and gas condensate absorption peak changes. These changes occur due to a combination of factors, which can include changes in pressure and/or temperature, and/or in the light source intensity variations, and/or in the small shifts in the wavelength and dark noise in the spectrometer(s), and/or in partial optical window fouling by deposits (which is similar to the scattering effects), and/or in the mixture of the multiphase flow.

To further improve measurement errors, the optical immersion probe may include optical fiber bundles that are treated to reduce the aging, solarization or darkening effect. However, in certain aspects, the external location of the light source and the optical spectroscopic detection components within the present embodiment of the optical immersion probe may allow for an improved system. This is because in such aspects, the light source may be easily modified or repaired without replacing the entire optical immersion probe and the probe's light source and detection components are not in direct contact with the high pressure and potentially high temperature multiphase flows.

As mentioned above, taking absorption peaks and baseline measurements, the optical attenuation due to the scattering effect of the multiphase fluid flowing within the well can be removed with reference to the baseline measurement. Scattering is an important factor for removal as the scattering effect is usually the most predominant error introduced in the liquid-fraction measurements of the flow. This is because the flow is multiphase, often including large amounts of gas bubbles and/or liquid droplets dispersed in the liquid and/or gas phase. However, liquid droplets, bubbles, density variations in the phases of the multiphase flow, and particles within the well all can contribute to the scattering effect. Each of the aforementioned factors, cause a deviation of the reflected radiation produced by the UV and IR light sources.

The scattering effect can be removed by subtracting the apparent absorption of water and oil mixture including the scattering effect away from the water absorption peak and the oil absorption peak. As previously discussed, one of the water absorption peaks is centered around 1450 nm at standard conditions of temperature and pressure (e.g., 20° C. and 100 kPa) and the oil-condensate absorption peak can be centered around 280 nm at standard conditions of temperature and pressure. The removal of the scattering effect from the measured total attenuation is exemplified in the following equation $$OD_{Measured}(\lambda) = OD_{Absorption}(\alpha_{water}, \alpha_{oil}; \lambda) + \\ OD_{Scattering}(\alpha_{water}, \alpha_{oil}; \lambda) \\ = \alpha_{water} OD_{1-mm}^{water}(\lambda) D + \alpha_{oil} OD_{1-mm}^{oil}(\lambda) D + \\ OD_{Scattering}(\alpha_{water}, \alpha_{oil}; \lambda)$$  (1)

where D is the optical path-length of the optical immersion probe, $\lambda$ is the measurement wavelength, $\alpha_{water}$ is the water fraction (across path D), $\alpha_{oil}$ is the oil fraction (across path D), $OD_{Measured}$ is the measured total attenuation, $OD_{Absorption}$ is the sum of water and oil absorptions, $OD_{Scattering}$ is the scattering attenuations of oil and water. $OD_{1-mm}^{water}(\lambda)$ and $OD_{1-mm}^{oil}(\lambda)$ are absorption spectra (calibration) measurements of water and oil samples across 1 millimeter (mm) optical path-length.

With an appropriate selection of the measurement wavelength bands in the UV and NIR range, the absorption of the gas phase in the multiphase flow can be made negligible (in equation 1) over a wide range of pressures and temperatures. This will make the gas condensate and water fraction measurement and hence the WLR measurement more robust. Accordingly, a wider WLR working range in terms of multiphase flow gas-volume-fraction (GVF) can be achieved by operating the optical immersion probe in the UV range (such that it is mainly sensitive to condensate/light oil absorption) and in the NIR range (such that it is mainly sensitive to water absorption).

Achieving the highest/a high water and condensate/light oil absorption contrast in separate UV and NIR broadband enables a better tolerance to the high levels of scattering due to entrained bubbles/droplets being present at large GVF, which is an especially important merit for measuring the WLR of high GVF wet-gas flows. In some embodiments, if desired, the optical immersion probe can allow the detection of the water phase only, e.g. by using only NIR radiation and detection. Similarly, if only gas condensate (light oil) is desired, only UV radiation and detection is utilized. Either wavelength band can be utilized when computing the WLR. The usage of both wavelength bands offers an improved WLR result with the scattering effect being removed.

For example, with the selection of the entire oil peak (or high absorption values near the oil peak) integration wavelength range being $\lambda_1$, oil off-peak integration range $\lambda_2$ (e.g. $\lambda_1$=250-320 nm, $\lambda_2$=320-400 nm for a light oil) where the water and gas are substantially non-absorptive, and with the selection of the entire water peak integration wavelength range $\lambda_4$=1300-1600 nm, water off-peak integration range $\lambda_3$=1200-1300 nm where the condensate-oil and gas are substantially non-absorptive, and because of the weak wavelength dependence of the scattering attenuation in the selected UV or NIR bands, we can derive from the above equation the following set of equations:

$$\begin{cases} \alpha_{water} D_{w,1} + \alpha_{oil} D_{o,1} = A_1 \\ \alpha_{water} D_{w,2} + \alpha_{oil} D_{o,2} = A_2 \end{cases}$$  (2)

where $D_{w,1}$, $D_{w,2}$, $D_{o,1}$, $D_{o,2}$, $A_1$ and $A_2$ are the appropriate broadband wavelength spectra integration values (with scattering removed). Each factor is expressed as follows:

$$D_{w,1} = D \lfloor \overline{OD_{1-mm}^{water}(\lambda_1)} - \overline{OD_{1-mm}^{water}(\lambda_2)} \rfloor \quad D_{o,1} = D \lfloor \overline{OD_{1-mm}^{oil}(\lambda_1)} - \overline{OD_{1-mm}^{oil}(\lambda_2)} \rfloor$$

$$D_{w,2} = D \lfloor \overline{OD_{1-mm}^{water}(\lambda_4)} - \overline{OD_{1-mm}^{water}(\lambda_3)} \rfloor \quad D_{o,2} = D \lfloor \overline{OD_{1-mm}^{oil}(\lambda_4)} - \overline{OD_{1-mm}^{oil}(\lambda_3)} \rfloor$$

$$A_1 = \overline{OD_{meas}(\lambda_1)} - \overline{OD_{meas}(\lambda_2)} \quad A_2 = \overline{OD_{meas}(\lambda_4)} - \overline{OD_{meas}(\lambda_3)}$$  (3)

These set of equations then are solved to calculate cross-path (D) water and oil fractions or holdups ($\alpha_{water}$, $\alpha_{oil}$) in the optical immersion probe. Subsequently, the water in liquid ratio (WLR), or water-cut, for a well-mixed liquid, then is calculated at any gas volume fraction (GVF) as:

$$WLR = \alpha_{water}/(\alpha_{water} + \alpha_{oil})$$  (4)

In addition, varying the flow gap, or path length of the probe according the flow condition can provide improvements in data collection. For example, for a single-path probe, increasing the gap to 1.5 mm and comparing the measurements with those collected at 1 mm may better assess the scattering effect. However, increasing the gap flow path to beyond 2 mm across which the light travels can decrease the linearity in the measurement if the total attenuation (scattering and absorption) across the gap increases. This is because a UV/NIR spectrometer normally have a good linearity range below OD=3, and a good linearity range between 1 mm-1.5 mm path-length can be achieved for water near the 1450 nm NIR peak, with absorption-only OD up to 1.6 to 2.4; the remaining linear-range OD budget (1.4 to 0.6) is needed to cover the likely baseline shift due to scattering attenuation. Similar linearity considerations should be made to the measurements at or near the oil absorption peak. Accordingly, beyond 2 mm may begin to exceed the linearity range of the spectrometer(s).

If the measured total absorption and scattering OD is kept within a linear range of spectrometers and the scattering baseline OD is removed, experimental results are able to provide a 5% error of the absolute WLR between the measured and the known amounts, for GVF=0 to 99.5% and WLR=0% to 100%.

In embodiments of the present invention, placement of the optical immersion probe can also be varied. In some embodiments, for instance, the optical immersion probe may be placed with the gap near the center of the well pipe or near the inner wall of the well pipe. If placement of the optical immersion probe and flow gap is near the pipe center, increasing the gap size during measurement aids in measuring the water-cut due to the higher GVF at the pipe center as the oil condensate/water build-up tends to be located along the pipe wall. However, in other embodiments, placement at the pipe center may increase attenuation due to the scattering effect, as more amount of the liquid droplets entrained in the gas phase is entering the flow gap. With increased scattering attenuation experienced at the pipe center and with a larger flow gap, the peak total absorptions of the flow can be dominated by the scattering that overwhelms the true absorptions that are extracted (in equations 2 and 3) to calculate oil and/or water fractions across the gap, hence the WLR (equation 4) is not the representative of the pipe average WLR. Placing the probe near a liquid-rich region of the pipe, such as near the inner wall of the pipe, may be advantageous for a representative WLR measurement, where true absorption effects at the selected wavelength band(s) of the oil/water liquid may dominate the flow scattering effect. Accordingly, placement of the optical immersion probe and the flow gap size can largely impact the determination and predictability of the WLR and, subsequently, flow rate measurements.

However, at higher GVF, the amount of water and/or oil in the multiphase flow is inherently lower, leading to less water and/or oil fraction across the probe flow gap, whereas lower GVF include increased water/oil amounts leading to increased water/oil fraction.

As can be interpreted from the aforementioned exemplary embodiments, placement of the optical immersion probe and variable gap lengths greatly affect the predictability of the oil and/or water fraction within a well, highly due to the combined scattering and/or absorption effects that may exceed the optical-density linearity range of optical spectrometer(s). Though an increased gap length can seem more unpredictable with the aforementioned method, in some embodiments a large flow path is still desirable, such as for a very high GVF wet-gas flow, or a gaseous flow containing water vapor or steam when water or steam quality detection is important, and where the optical-density resolution of optical spectrometer(s) is limited. Such embodiments are described in a cross-pipe NIR/UV liquid flow detection in commonly owned Great Britain Patent Number GB 2426579. Decreasing the flow gap to below 0.2 mm can also decrease the WLR measurement accuracy as an insufficient amount of liquid sample is allowed to pass through the gap. Accordingly, a calculated WLR may not be a sufficiently representative estimate of the pipe average WLR.

Figure 3A:
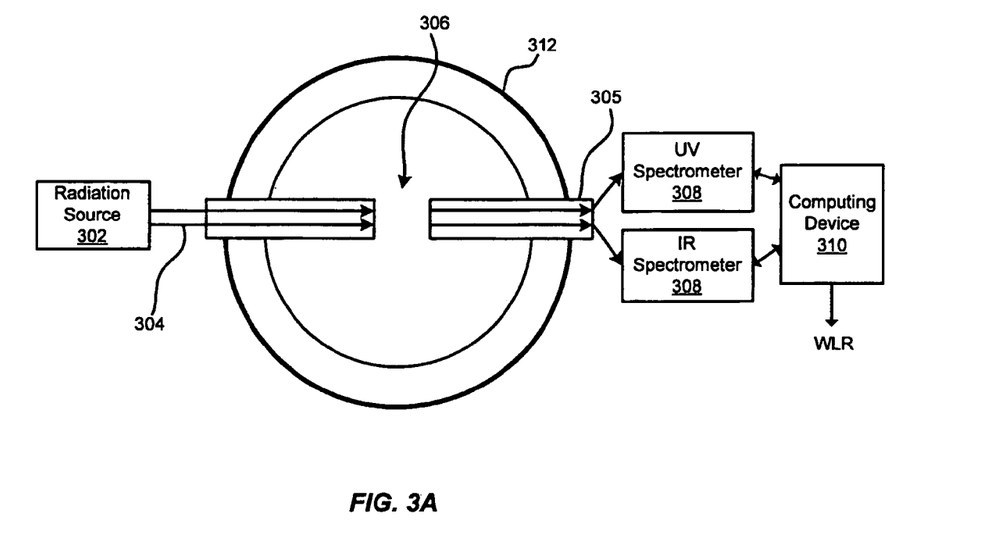
FIG. 3A provides a cross-pipe configuration for an optical immersion probe, in accordance with an embodiment of the present invention.
Figure 3B:
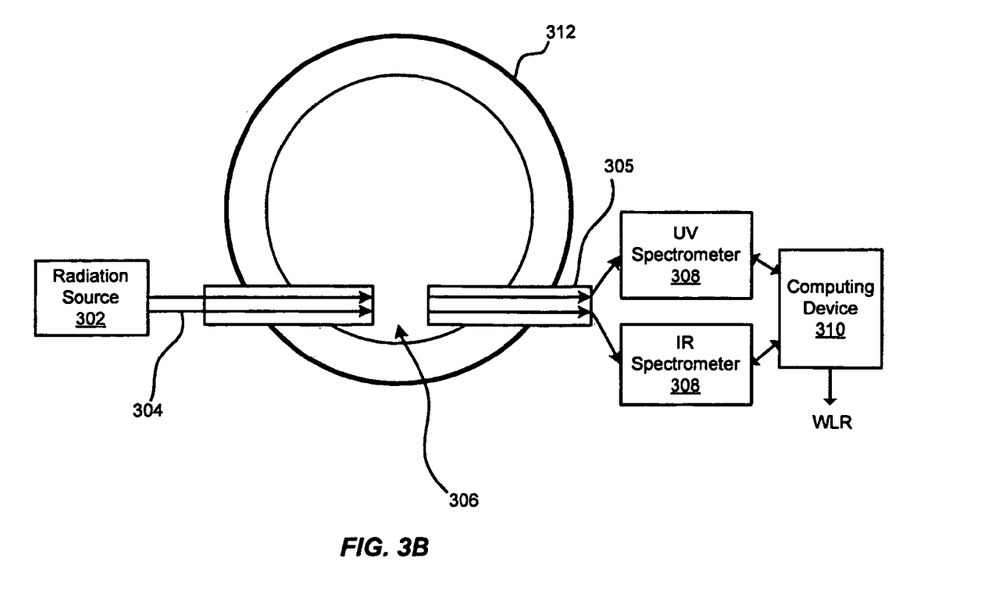
FIG. 3B provides an alternative cross pipe configuration for an optical immersion probe, in accordance with an embodiment of the present invention.

Referring now to FIGS. 3A-3B, various alternative embodiments of configuring the optical immersion probe position are illustrated. In some embodiments of the present invention, the optical immersion probe may includes a light source 302, light-delivery optical fiber bundles and optics 304, a flow gap 306, light-collection optical fiber bundles and optics 305, one or more spectrometers 308 and a computing device 310 for spectral analysis. As previously discussed, placement of the optical immersion probe and the flow gap 306 provides improved results for estimating water and/or oil fraction across the gap and the WLR of a multiphase flow. When analyzing the multiphase flow, the optical immersion probe can be positioned so that the flow gap 306 is near the wall or, alternatively, near the center of a flow pipe 312. As shown in FIG. 3A, the optical immersion probe is positioned so that the gap 306 is centrally located within the pipe 312. Such a configuration can be useful when measuring multiphase flows having very high GVF. In such an embodiment, the gap separation length of the optical immersion probe can be varied, dependent on the GVF of the wet-gas or a gaseous steam flow. Accordingly, for very high GVF (e.g., >99%), the gap length of the optical immersion probe can be increased to measure across the diameter of the pipe.

In flows having lower GVF, improved liquid-fraction and hence WLR measurement can be made by taking broadband optical attenuation readings closer to the pipe wall due to localized liquid phase (e.g., condensate and water) buildup along the wall. Such an embodiment is illustrated in FIG. 3B. The aforementioned liquid phase build-up provides decreased attenuation as less scattering from gas bubbles or liquid droplets is captured when radiation is transmitted across the flow gap in a primarily liquid mixture. Accordingly, attenuation occurs due to liquid-droplet scattering but primarily due to absorption or liquid-fraction variations; the latter is primarily a function of the relative proportions of water, light-oil and/or inhibitor (e.g., Methanol) in the liquid mixture. In an alternative embodiment, the aforementioned configurations can be useful for measuring flows in horizontal flow pipes, where the phases of the multiphase flows are effectively separated due to gravity.

Figure 4:
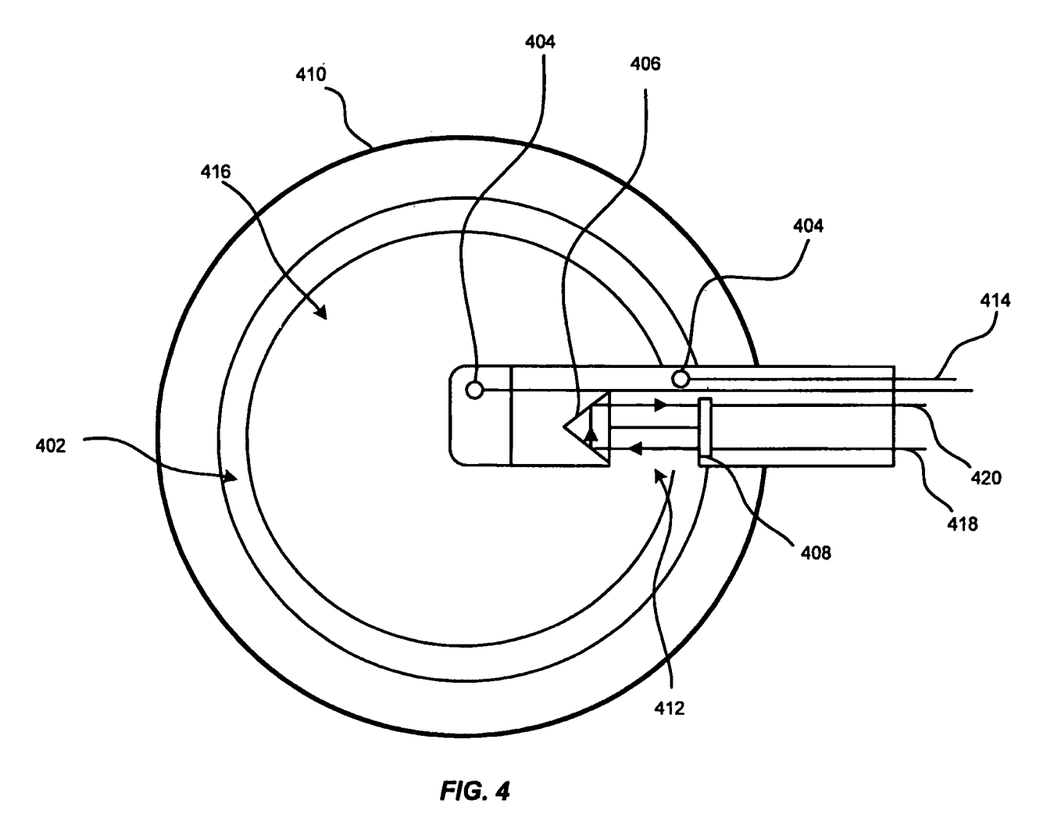
FIG. 4 provides an alternative configuration for an optical immersion probe, in accordance with an embodiment of the present invention.

Referring now to FIG. 4, swirling the wet-gas can also improve readings measured by the optical immersion probe. Utilizing centrifugal force imposed by a swirl generation means, such as at the upstream of a constricted region called a Venturi, the multiphase flow (e.g., gas and liquid mixture) can be separated to form a liquid layer 402 on the inner walls of the pipe 410 and a gas core 416 in the center of the pipe 410. In a throat section of the Venturi, there a reduced cross-section of the pipe 410. At an upstream pipe section of this reduced cross-section, the multiphase flow can be induced to swirl through a helical insert, a tangential flow entry into the upstream pipe or a vane assembly shaped and positioned to induce a centrifugal force in the multiphase flow. Additionally, in the constricted portion of the pipe, the centrifugal acceleration is higher than in larger cross-sectional regions of the upstream pipe, which allows for a better gas-liquid separation, hence a gas core 416 with less entrained liquid droplets, and a liquid layer 402 with less gas entrainment being displaced onto the wall of the pipe 410. With such a liquid layer in these constricted sections, the liquid phase of the multiphase flow can be more easily characterized through data collected in the separated liquid layer 402 by the probe. For example, the optical immersion probe can be situated in the pipe 410 to take measurements across only gas and/or only fluid portions of the mixture, thereby even further decreasing attenuation due to scattering and other factors.

The swirling technique can also be utilized to take further measurements by an optical immersion probe that includes additional sensing means, such as pressure ports 404. As previously discussed, the swirling of the wet gas allows for separation of the gas layer 416 and liquid layer 402. Accordingly, with additional pressure ports 404 added along the optical immersion probe body and properly aligned facing the flow, the axial-direction impact pressures of each respective phase can be measured. As previously discussed, a centrifugal force is applied to the multiphase flow, causing the flow to separate to form an axisymmetrical phase distribution. The different phases of the flow are then effectively separated, having the liquid phase portion displaced in a layer along the inner pipe wall, and the gas phase portion filling the central region of the pipe. The ports 404 can include pressure sensors attached to pressure sensing lines 414, which measure the dynamic impact pressure of each respective phase of the flow relative to a static pressure measured separately on the probe or at the pipe wall.

In some embodiments, the additional pressure ports 404 are added to the optical immersion probe portion near the center of the pipe ($p_c$) for measuring gas phase and to the probe portion near the wall of the pipe ($p_w$) for measuring liquid phase. The axial movement of theses phases against the pressure sensors allows for the measurement of impact, or dynamic pressure of the gas ($\Delta P_G$). The impact pressure at the pipe center is expressed as:

$$\Delta P_G = p_c - p_s \approx \frac{1}{2} \rho_G u_G^2 \qquad (5)$$

Similarly, the impact pressure of the liquid ($\Delta P_L$) measured near the pipe wall is:

$$\Delta P_L = p_w - p_s \approx \frac{1}{2} \rho_L u_L^2 \qquad (6)$$

These impact pressures are utilized to derive the gas flow velocity ($u_G$) and liquid flow velocity ($u_L$) within the pipe 410. In some embodiments, the gas and liquid densities ($\rho_G$, $\rho_L$) are known, such as through a sample measurements. In other embodiments, the densities are measured independently, such as through a micro-electro-mechanical MEMs densitometer or mini Coriolis meter(s), which take gas and/or liquid density measurements along the pressure tubing lines 414. As previously mentioned, the ports 404 can be attached to pressure lines 414, which run along the length of the optical immersion probe, away from the optical elements for determining liquid fractions. The single-path optical probe has a flow gap 412 that cover the entire thickness of the liquid layer 402 and some part of the gas core 416. An NIR/UV light beam is delivered through optic fiber bundle 418, through an optical window 408, and is transmitted into the flow in the gap 412. The light beam, after attenuation by the flow, is reflected by a prism 406 or similar reflective element, and delivered to spectrometer(s) through another optic fiber bundle 420 for spectral analysis. As discussed in previous paragraphs, the oil and water fractions ($\alpha_{oil}$, $\alpha_{water}$) in the flow gap can be determined, and also the WLR.

Finally, the flow rates of each respective phase are derived from the gas and liquid flow velocities ($u_G$, $u_L$) and the phase fractions ($\alpha_{oil}$, $\alpha_{water}$) and the cross-sectional area of the pipe (A). The flow rates for the gas, oil and water, respectively, are analytically represented as:

$$q_G = u_G(1-\alpha_L)A \text{ (gas)} \quad (7)$$

$$q_o = u_L \alpha_{oil} A \text{ (oil)} \quad (8)$$

$$q_w = u_L \alpha_{water} A \text{ (water)} \quad (9)$$

With these measurements, the gas, water and oil fractions and flow rates within the well can be determined. Such measurements can also aid in determining whether or not inhibitors or other flow assurance means are needed to avoid hydrate plugging and/or corrosion within the well. Additionally, the aforementioned measurements can aid in determining if there are onset of first water or formation- or injection-water breakthrough within the well pipe, which is determined by the increased WLR and/or water flow rate.

Referring again to FIG. 4, the optical immersion probe can be adjusted axi-symetrically to gather data from each separated phase and to measure the pressure/flow velocities at different locations within the pipe. In some embodiments, the optical immersion probe can extend across a large portion of or the entire well pipe and include more than one pressure port 404. However, it is understood that the optical immersion probe can also contain only one pressure port 404. In such an embodiment, the optical immersion probe can be traversed so that the pressure port is used to identify each phase of the flow by taking impact pressure and/or fluid density measurements. After swirling the mixture, different impact pressures and/or fluid densities may be experienced in the gas phase near the center of the pipe and in the liquid phase located near the pipe wall. With the aforementioned measurements the amount of gas and the liquid (condensate and/or water) being produced by the well can be calculated based on the measured spatial profiles of impact pressures and/or fluid densities over a specified period of time.

Figure 5:
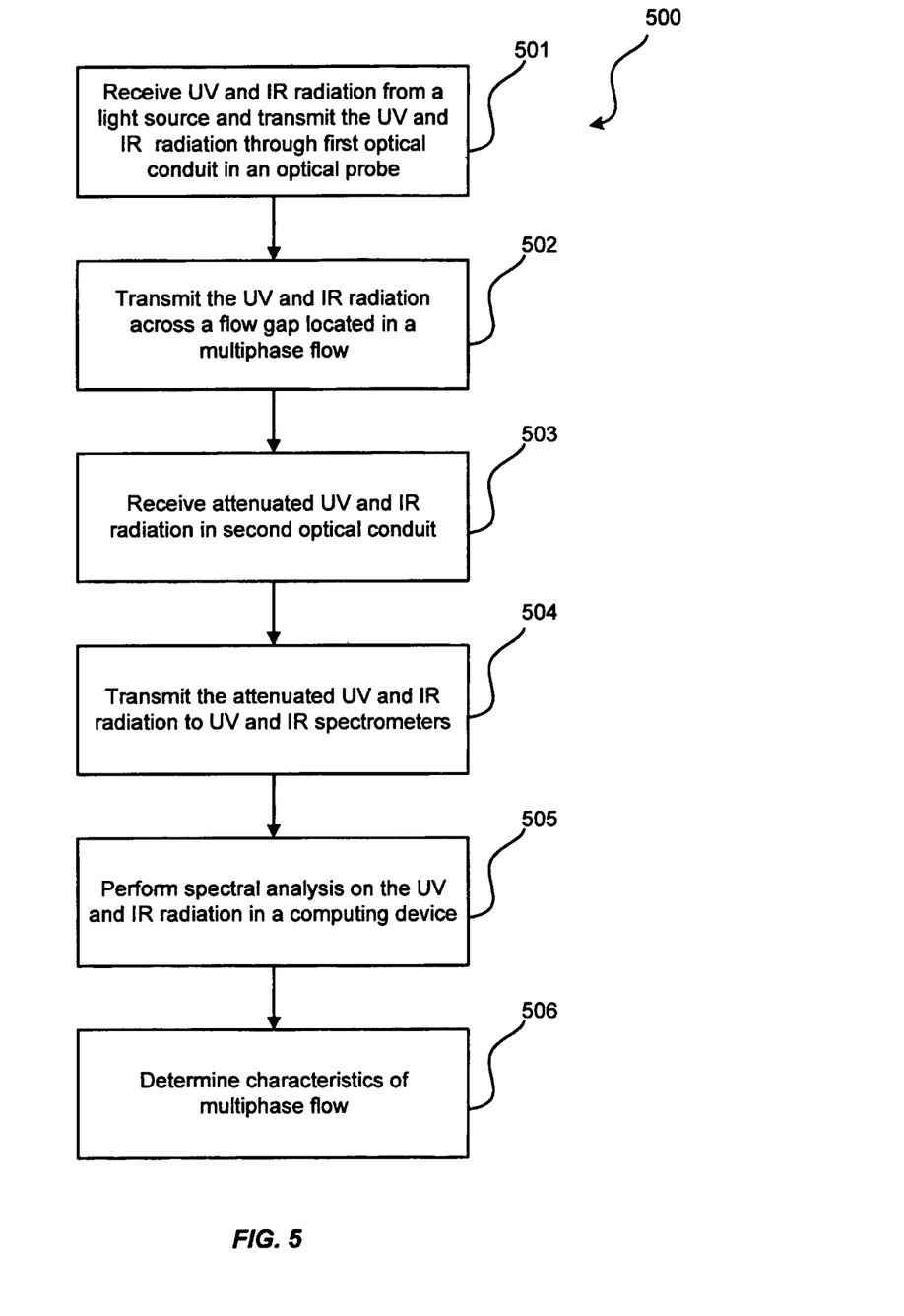
FIG. 5 provides a flow chart for characterization of a multiphase flow, in accordance with an embodiment of the present invention.

FIG. 5 provides a method 500 for utilizing an optical immersion probe to determine the characteristics of the multiphase flow as is described with reference to FIG. 4.

In step 501, after swirling the mixture, light sources can provide radiation to transmitting optical fibers 418 coupled to the optical immersion probe. The light sources are located outside the optical immersion probe and can be coupled to the optical immersion probe through the optical fiber bundles 418. The light source can emit pulsed light over set time intervals, or continuous light over a set time interval.

In step 502, UV and NIR light beams can then be sent by a transmitting optical fiber bundle 418 through an optical window 408 and across a portion of the layer of liquid 402 and a portion of the layer of gas 416 through a flow gap 412. When the light passes through the multiphase flow, the light is attenuated, dependent on the contents of oil, water, and gas. Alternatively, the optical immersion probe can be repositioned within the pipe 410 in order to gather only liquid or only gas samples. The swirling of the multiphase flow can provide better results when positioning the optical immersion probe to collect measurements on each specific phase.

In step 503, the attenuated light are reflected by a prism 406, or similar reflective element, and are received by a receiving optical fiber bundle 420, which is coupled to both a UV and IR spectrometer located outside the optical immersion probe. Both receiving and transmitting optical fiber bundles can include more than one bundle, which is specifically treated for UV and IR transmission. Additionally, though a single path radiation probe is preferably utilized to describe method 500, it is understood that a double path radiation probe can also be utilized.

In step 504, the attenuated light is transmitted to spectrometer(s) (not shown) through the receiving optical bundle 420. The optical bundles can be treated to maximize transmittance of each respective type of radiation. In some embodiments, the bundle can be treated to increase transmittance of more than one type of radiation. The bundle can also be pre-treated to withstand extreme temperatures and pressures, which may be experienced in the oil or gas wells.

In step 505, the spectrometers then perform UV and IR spectral analysis to determine the water and oil fractions and then the water-in-liquid ratio through characteristics of the measured absorption peaks. For example, significant changes in both the IR and UV absorption peaks above a baseline shifted by dispersed-phase scattering effects could indicate that large amounts of other constituents exist in the wet-gas and water of liquid phase. Some constituents can include hydrate inhibitors, such as used in deepwater oil/gas wells to prevent plugging in the well pipes. Additionally in step 505, the gas fraction can be determined, dependent upon the measured thickness of the separated liquid layer 402.

Accordingly, in step 506, by determining the attenuation and peak shifts of the absorption spectra in the liquid phase of the multiphase flow, the flow can be further characterized to determine whether there is water and/or oil in the gas flow, such as in natural gas wells, or whether inhibitor is necessary to prevent hydrates and/or corrosion. The concept of characterizing, or measuring properties of a swirled flow is described in commonly owned U.S. Pat. No. 7,650,799B2.

As mentioned previously, swirling the multiphase flow allows the liquid layer 402 to be essentially free of gas bubbles, which greatly reduces the optical scattering attenuation. The reduced amount of liquid droplets in the gas core also reduces the scattering attenuation. Accordingly, swirling the wet-gas will allow for a better linear range of measured optical attenuation data and an increased measurement range in the liquid layer 402 thickness and the WLR in terms of a wider GVF working range.

To calculate this water-in-liquid ratio (WLR), the optical immersion probe can allow for interrogation across the entire separated liquid layer 402 to measure its content. This interrogation provides a liquid fraction $\alpha_L = \alpha_{oil} + \alpha_{water}$, where $\alpha_{oil}$ is the oil fraction and $\alpha_{water}$ is the water fraction, and WLR is equal to $\alpha_{water}/\alpha_L$.

A number of variations and modifications of the disclosed embodiments can also be used. For example, the optical immersion probe can include only an NIR light source together with the pressure ports. Alternatively, the optical immersion probe can include only the NIR/UV light sources and no pressure ports. Furthermore, measurements can be taken across different wavelength bands than the UV, Visible and IR broadband absorption spectra, if desired. Accordingly, light sources providing radiation in those different wavelength bands can also be utilized with the optical immersion probe. The optical immersion probe can vary in flow-gap size so that it extends across the diameter of a pipe, or only a portion of the diameter. The optical immersion probe can be fixed at one position in a pipe, or can be traversed to vary its measurement (i.e., flow gap and sensor) position along a chord or a diameter of the pipe. In the embodiment where the probe traverses the pipe, the probe can permit the measurements of water fraction, oil fraction and WLR profiles along a pipe diameter, hence a determination of cross-pipe averaged water fraction, oil fraction and WLR. In any of the embodiments, the pipe can include a downhole well, a subsea or a surface well, or a downhole, subsea or surface production transportation pipeline, or a bypass or a sampling line of the pipeline, or a sampling line of a downhole or surface tool.

Specific details are given in the above description to provide a thorough understanding of the embodiments. However, it is understood that the embodiments may be practiced without these specific details.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

While the principles of the disclosure have been described above in connection with specific apparatuses and methods, it is to be clearly understood that this description is made only by way of example and not as limitation on the scope of the disclosure.

What is claimed is:

1. An optical immersion probe for analyzing a multiphase flow in a pipe, the optical probe comprising:
    a housing;
    one or more first optical conduits, adapted to carry ultraviolet radiation and/or infrared radiation from one or more radiation sources at a first end to a second end;
    a flow gap across which the ultraviolet radiation and/or infrared radiation is transmitted, wherein the flow gap begins at the second end of the one or more first optical conduits and is configured to operatively engage the multiphase flow in the pipe;
    one or more second optical conduits adapted to receive at least a portion of the ultraviolet radiation and/or infrared radiation, and transmit at least a portion of the received ultraviolet radiation and/or infrared radiation to one or more spectrometers for spectral analysis; and
    one or more pressure sensors for measuring impact pressure of at least one of the phases in the multiphase flow, wherein:
        the ultraviolet radiation and/or infrared radiation is attenuated through absorption and/or scattering by the multiphase flow in the flow gap;
        the multiphase flow is analyzed through the ultraviolet radiation and/or infrared radiation attenuation determined by the spectrometers; and
        the probe includes at least two pressure sensors divided by a distance equal to the pipe radius.

2. The optical immersion probe for analyzing a multiphase flow in a pipe, as set out in claim 1, further comprising: one or more pressure lines for use with measuring a density of one or more phases of the multiphase flow.

3. The optical immersion probe for analyzing the multiphase flow in the pipe as recited in claim 2, further comprising:
    one or more ports for exposing the one or more pressure sensors through the one or more pressure lines to the multiphase flow.

4. The optical immersion probe for analyzing the multiphase flow in the pipe as recited in claim 2, further comprising:
    a temperature sensor for determining the flow thermodynamic conditions of the multiphase flow.

5. A method for analyzing a multiphase flow in a pipe with an optical immersion probe as recited in claim 1, wherein the multiphase flow includes at least a gas phase and a liquid phase, the liquid phase comprising one or more of water and oil condensate, the method comprising:
    swirling the multiphase flow to separate the gas and liquid phases of the flow, wherein the swirling comprises applying a centrifugal force;
    carrying ultraviolet and/or infrared radiation from one or more light sources in one or more first optical conduits;
    transmitting the ultraviolet and/or infrared radiation from the one or more first optical conduits across a flow gap, wherein the flow gap begins at the second end of the one or more first optical conduits and is configured to operatively engage the multiphase flow;
    reflecting the ultraviolet and/or infrared radiation on a reflective element, wherein the reflective element is located a distance across the flow gap from the one or more first optical conduits;
    receiving at least a portion of the reflected ultraviolet and/or infrared radiation in a second optical conduit;
    transmitting at least a portion of the received ultraviolet and/or infrared radiation to one or more optical spectrometers for spectral analysis; and
    analyzing the multiphase flow in a computing device to determine characteristics of the multiphase flow, wherein:
        the ultraviolet radiation and/or infrared radiation is attenuated through absorption and/or scattering when in contact with the multiphase flow, and
        the multiphase flow is analyzed through the ultraviolet and/or infrared attenuation determined by the spectrometers.

6. The method for analyzing the multiphase flow in the pipe with the optical immersion probe as recited in claim 5, wherein the one or more spectrometers includes an infrared spectrometer operating at the 900-2550 nanometer range.

7. The method for analyzing the multiphase flow in the pipe with the optical immersion probe as recited in claim 5, wherein the one or more spectrometers includes an ultraviolet spectrometer operating at the 200-800 nanometer range.

8. The method for analyzing the multiphase flow in the pipe with the optical immersion probe as recited in claim 5, wherein the one or more radiation sources are located external to and separate from the optical immersion probe.

9. The method for analyzing the multiphase flow in the pipe with the optical immersion probe as recited in claim 5, wherein the one or more radiation sources include a first radiation source capable of emitting a continuous light spectrum in the ultraviolet to visible range.

10. The method for analyzing the multiphase flow in the pipe with the optical immersion probe as recited in claim 5, wherein the one or more radiation sources include a second radiation source capable of emitting a continuous light spectrum in the visible to near infrared range.

11. A method for analyzing a multiphase flow in a pipe with an optical immersion probe as recited in claim 1, the method comprising:

applying centrifugal force to the multiphase flow, wherein the centrifugal force effectively separates one or more phases of the flow;

carrying ultraviolet and/or infrared radiation from one or more light sources in one or more first optical conduits;

transmitting the ultraviolet and/or infrared radiation from the one or more first optical conduits across a flow gap, which is configured to operatively engage at least one phase of the multiphase flow;

reflecting the ultraviolet and/or infrared radiation on a reflective element, wherein the reflective element is located a distance across the flow gap from the one or more first optical conduits;

receiving at least a portion of the reflected ultraviolet and/or infrared radiation in a second optical conduit; and transmitting at least a portion of the received ultraviolet and/or infrared radiation to one or more optical spectrometers for spectral analysis.

12. The method for analyzing the multiphase flow in the pipe with the optical immersion probe as recited in claim 11, further comprising:

exposing one or more pressure sensors to the multiphase flow; and measuring the impact pressure of the one or more phases in the multiphase flow with the one or more pressure sensors.

13. The method for analyzing the multiphase flow in the pipe with the optical immersion probe as recited in claim 11, wherein the one or more first optical conduits is an optical fiber bundle for transmitting radiation.

14. The method for analyzing the multiphase flow in the pipe with the optical immersion probe as recited in claim 11, wherein the one or more second optical conduits is an optical fiber bundle for receiving radiation.

15. The method for analyzing the multiphase flow in the pipe with the optical immersion probe as recited in claim 11, wherein the one or more light sources include a first light source capable of emitting a continuous light spectrum in the broadband ultraviolet to visible range.

16. The method for analyzing the multiphase flow in the pipe with the optical immersion probe as recited in claim 11, wherein the one or more light sources include a second light source capable of emitting a continuous light spectrum in the broadband visible to infrared range.

17. The optical immersion probe for analyzing the multiphase flow in the pipe as recited in claim 1, further comprising a reflective element for reflecting the ultraviolet radiation and/or the infrared radiation across the multiphase flow from the one or more first optical conduits to the one or more second optical conduits.

18. The optical immersion probe for analyzing the multiphase flow in the pipe as recited in claim 1, further comprising:

an optical window through which to send and receive the ultraviolet radiation and/or infrared radiation.

19. The optical immersion probe for analyzing the multiphase flow in the pipe as recited in claim 1, further comprising:

an optical window through which to send and receive the ultraviolet radiation and/or infrared radiation, wherein the optical window is collimated.

20. The optical immersion probe for analyzing the multiphase flow in the pipe as recited in claim 1, further comprising:

a temperature sensor for determining the flow thermodynamic conditions of the multiphase flow.

\* \* \* \* \*